(12) United States Patent
Nishina et al.

(10) Patent No.: US 10,964,003 B2
(45) Date of Patent: Mar. 30, 2021

(54) IMAGE PROCESSING APPARATUS, IMAGE PROCESSING METHOD, AND PROGRAM

(71) Applicant: OMRON Corporation, Kyoto (JP)

(72) Inventors: Yuki Nishina, Kyoto (JP); Yoshinori Konishi, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 16/347,841

(22) PCT Filed: Oct. 24, 2017

(86) PCT No.: PCT/JP2017/038330
§ 371 (c)(1),
(2) Date: May 7, 2019

(87) PCT Pub. No.: WO2018/131252
PCT Pub. Date: Jul. 19, 2018

(65) Prior Publication Data
US 2019/0340735 A1 Nov. 7, 2019

(30) Foreign Application Priority Data
Jan. 12, 2017 (JP) .............................. JP2017-003102

(51) Int. Cl.
*G06T 5/50* (2006.01)
*G06T 5/00* (2006.01)
(Continued)

(52) U.S. Cl.
CPC ................ *G06T 5/50* (2013.01); *G06T 5/003* (2013.01); *G06T 7/44* (2017.01); *G06T 11/003* (2013.01);
(Continued)

(58) Field of Classification Search
CPC .. G06T 5/50; G06T 7/44; G06T 5/003; G06T 11/003; G06T 2207/20212;
(Continued)

(56) References Cited

U.S. PATENT DOCUMENTS

2003/0215051 A1* 11/2003 Suzuki ................. A61B 6/0478
378/19
2006/0104410 A1 5/2006 Sauer et al.
(Continued)

FOREIGN PATENT DOCUMENTS

JP H10-005210 A 1/1998
JP 2004-113271 A 4/2004
(Continued)

OTHER PUBLICATIONS

Cant Jeroen et al, "Modeling blurring effects due to continuous gantry rotation, Application to region of interest tomography", Medical Physics, May 2015, pp. 2709-2717, vol. 42, No. 5, Melville, NY, US; Relevance is indicated in the EESR dated Jun. 3, 2020.
(Continued)

*Primary Examiner* — Christopher M Brandt
(74) *Attorney, Agent, or Firm* — Metrolex IP Law Group, PLLC

(57) ABSTRACT

A reconstruction processing unit includes a filtering unit which applies a filter for correcting a motion blur attributable to a relative movement of an image pickup system and an object to a transmission image when performing an operation of back-projecting a pixel on the transmission image to a cell on a reconstructed image. A filter that the filtering unit uses when a pixel on a first transmission image is back-projected to a first cell on the reconstructed image is different from a filter that the filtering unit uses when the pixel on the first transmission image is back-projected to a
(Continued)

second cell existing at coordinates that differ from those of the first cell.

7 Claims, 15 Drawing Sheets

(51) Int. Cl.
    *G06T 11/00*     (2006.01)
    *G06T 7/44*     (2017.01)
    *A61B 6/03*     (2006.01)

(52) U.S. Cl.
    CPC ..... *A61B 6/032* (2013.01); *G06T 2207/20212* (2013.01)

(58) Field of Classification Search
    CPC . G06T 2211/412; G06T 11/005; A61B 6/032; A61B 6/5235
    See application file for complete search history.

(56) References Cited

U.S. PATENT DOCUMENTS

| | | |
|---|---|---|
| 2008/0044076 A1 | 2/2008 | Spies |
| 2013/0177225 A1 | 7/2013 | Zamyatin et al. |
| 2014/0029819 A1 | 1/2014 | Zeng et al. |
| 2015/0243045 A1* | 8/2015 | Ra .................... A61B 6/032 382/131 |
| 2016/0300369 A1* | 10/2016 | Silver .................. G06T 5/20 |

FOREIGN PATENT DOCUMENTS

| | | |
|---|---|---|
| JP | 2005-021345 A | 1/2005 |
| JP | 2008-505678 A | 2/2008 |
| JP | 2011-194010 A | 10/2011 |
| JP | 2014-023936 A | 2/2014 |
| JP | 2016-198504 A | 12/2016 |
| WO | 2013/105583 A1 | 7/2013 |

OTHER PUBLICATIONS

Extended European search report (EESR) dated Jun. 3, 2020.
An English translation of the International Search Report ("ISR") of PCT/JP2017/038330 dated Jan. 23, 2018.
An English translation of the Written Opinion("WO") of the International Searching Authority of PCT/JP2017/038330 dated Jan. 23, 2018.
The English translation of the International Preliminary Report on Patentability (Chapter II) dated Jul. 18, 2019 in the International Application No. PCT/JP2017/038330.
Korean Office Action dated Aug. 27, 2020 for the counterpart Korean patent application.

* cited by examiner

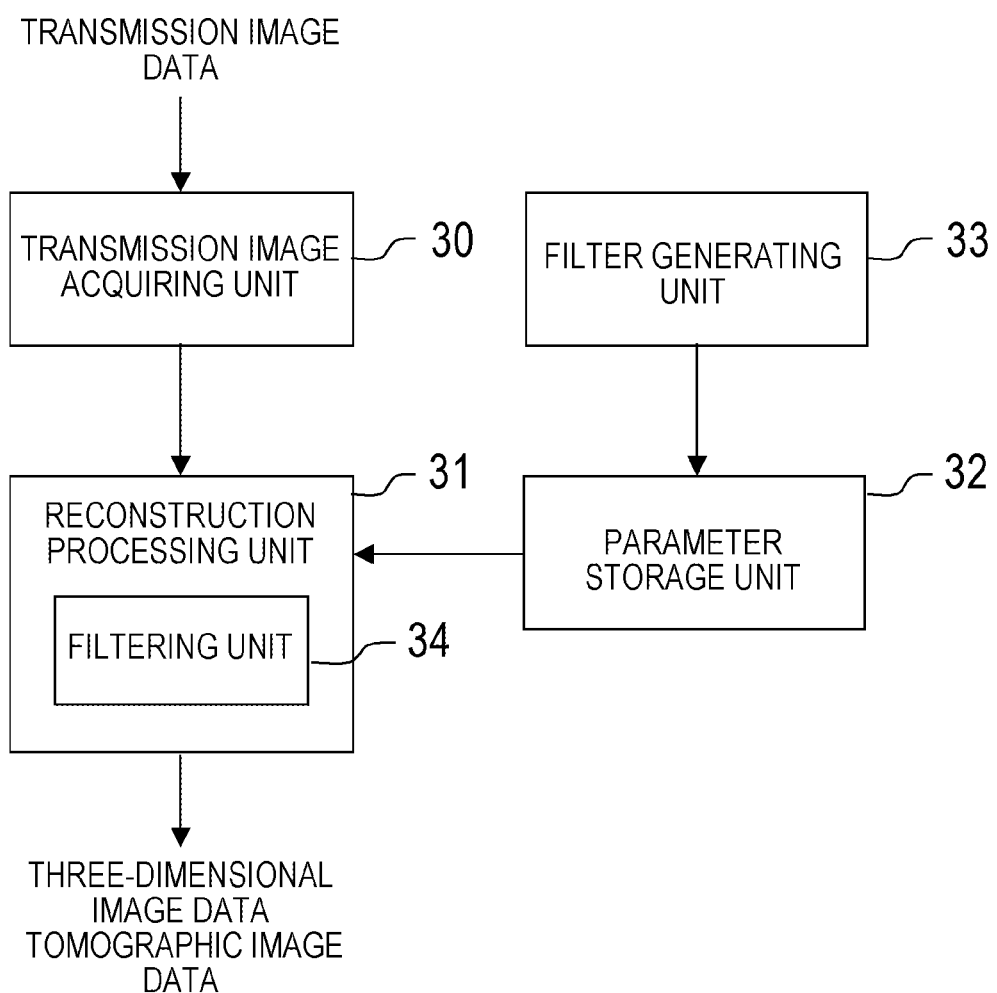

FIG. 5
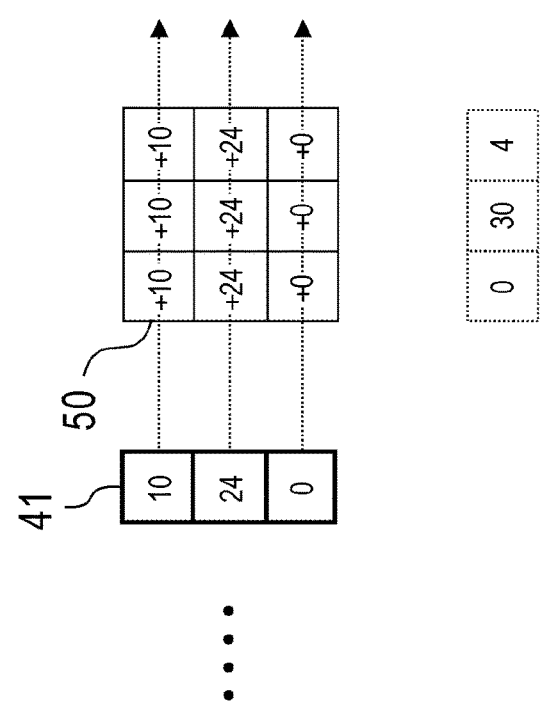
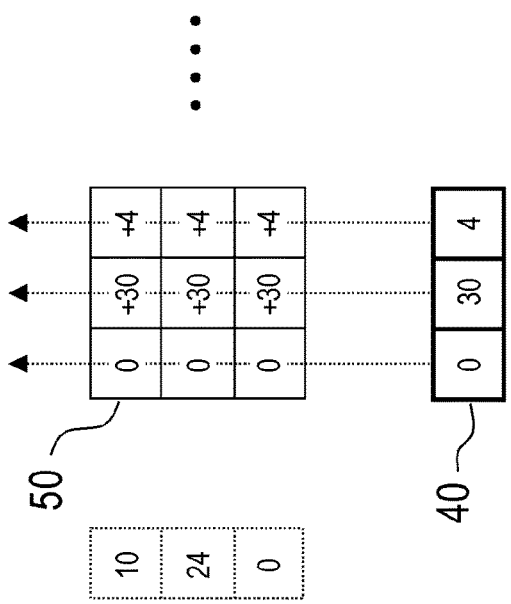

FIG.8

| IMAGE PICKUP CONDITIONS | EXPOSURE START ANGLE [rad] | EXPOSURE END ANGLE [rad] | ROTATIONAL SPEED [rad/s] | ROTATION DIRECTION |
|---|---|---|---|---|
| PROJECTION #0 | 0 | $\pi/4$ | v | CLOCKWISE |
| PROJECTION #1 | $\pi/4$ | $2\pi/4$ | v | CLOCKWISE |
| PROJECTION #2 | $2\pi/4$ | $3\pi/4$ | v | CLOCKWISE |
| PROJECTION #3 | $3\pi/4$ | $\pi$ | v | CLOCKWISE |
| PROJECTION #4 | $\pi$ | $5\pi/4$ | v | CLOCKWISE |
| PROJECTION #5 | $5\pi/4$ | $6\pi/4$ | v | CLOCKWISE |
| PROJECTION #6 | $6\pi/4$ | $7\pi/4$ | v | CLOCKWISE |
| PROJECTION #7 | $7\pi/4$ | $2\pi$ | v | CLOCKWISE |

FIG. 9

MOTION BLURS

| IMAGE PICKUP CONDITIONS | y COORDINATE OF CELL | x COORDINATE OF CELL | | |
|---|---|---|---|---|
| | | x=0 | x=1 | x=2 |
| PROJECTION #0 | y=0 | PSF000 | PSF010 | PSF020 |
| | y=1 | PSF001 | PSF011 | PSF021 |
| | y=2 | PSF002 | PSF012 | PSF022 |
| PROJECTION #1 | y=0 | PSF100 | PSF110 | PSF120 |
| | y=1 | PSF101 | PSF111 | PSF121 |
| | y=2 | PSF102 | PSF112 | PSF122 |
| PROJECTION #2 | y=0 | PSF200 | PSF210 | PSF220 |
| | y=1 | PSF201 | PSF211 | PSF221 |
| | y=2 | PSF202 | PSF212 | PSF222 |
| .. | .. | .. | .. | .. |
| PROJECTION #7 | y=0 | PSF700 | PSF710 | PSF720 |
| | y=1 | PSF701 | PSF711 | PSF721 |
| | y=2 | PSF702 | PSF712 | PSF722 |

MOTION BLUR CORRECTION FILTERS

| IMAGE PICKUP CONDITIONS | y COORDINATE OF CELL | x COORDINATE OF CELL | | |
|---|---|---|---|---|
| | | x=0 | x=1 | x=2 |
| PROJECTION #0 | y=0 | h000 | h010 | h020 |
| | y=1 | h001 | h011 | h021 |
| | y=2 | h002 | h012 | h022 |
| PROJECTION #1 | y=0 | h100 | h110 | h120 |
| | y=1 | h101 | h111 | h121 |
| | y=2 | h102 | h112 | h122 |
| PROJECTION #2 | y=0 | h200 | h210 | h220 |
| | y=1 | h201 | h211 | h221 |
| | y=2 | h202 | h212 | h222 |
| .. | .. | .. | .. | .. |
| PROJECTION #7 | y=0 | h700 | h710 | h720 |
| | y=1 | h701 | h711 | h721 |
| | y=2 | h702 | h712 | h722 |

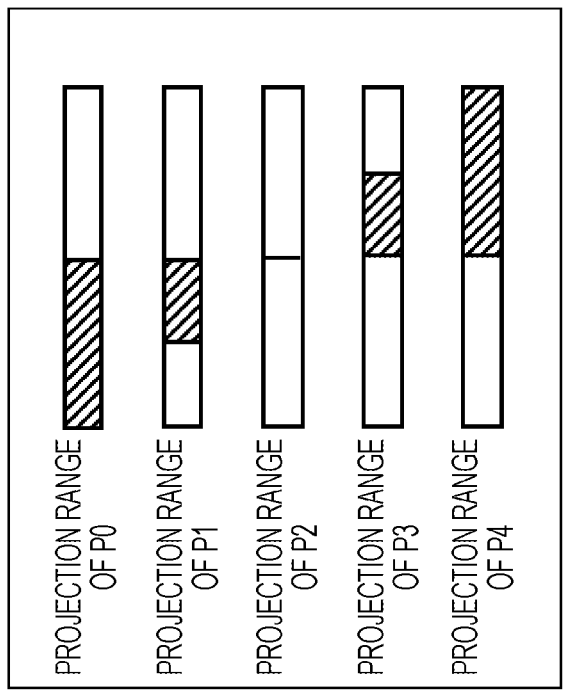
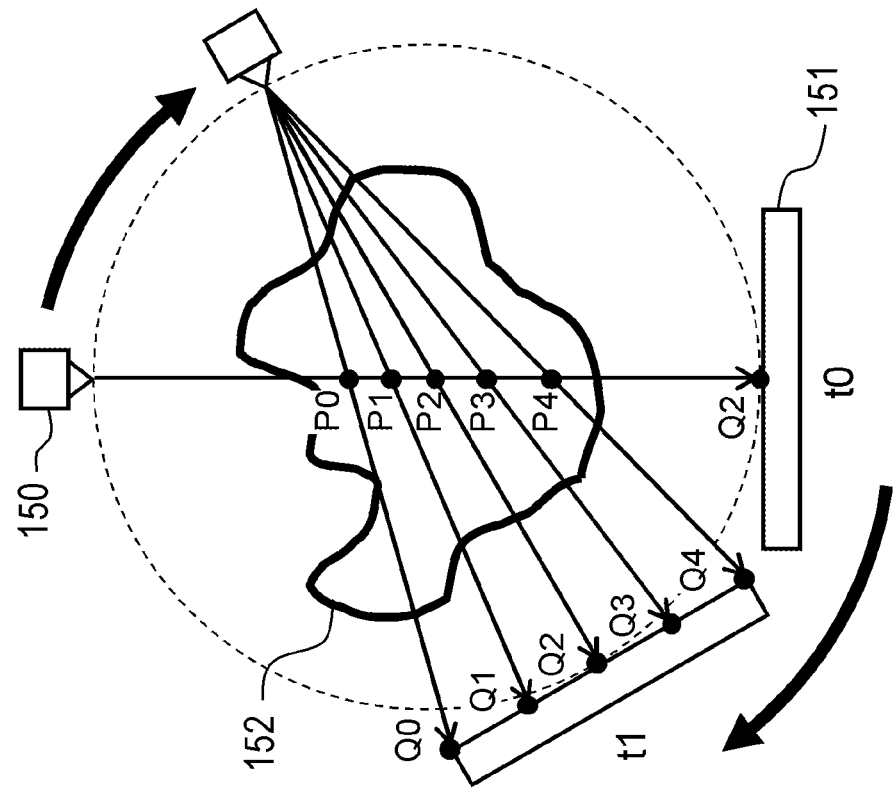

IMAGE PROCESSING APPARATUS, IMAGE PROCESSING METHOD, AND PROGRAM

TECHNICAL FIELD

The present invention relates to a technique for reconstructing a three-dimensional image of an object from a plurality of transmission images.

BACKGROUND ART

As a method for obtaining a three-dimensional image or a tomographic image of the inside of an object, a technique referred to as a CT (Computed Tomography) scan or simply CT has been known. X-ray CT using X-rays is being commercially utilized in medical examination apparatuses and industrial inspection apparatuses.

In X-ray CT, an object is arranged between a light source (an X-ray source) and a detector arranged so as to face each other, and a plurality of transmission images (also referred to as projection data) are photographed by the detector while changing X-ray projection directions. Subsequently, on the basis of the plurality of transmission images with different projection directions, an inverse problem is solved by computer processing to reconstruct a three-dimensional image of the inside of the object. While a so-called Stop & Go system in which photography of a transmission image and a change to the projection direction (a relative movement of the object and the detector) are repetitively alternated has been the mainstream in conventional X-ray CT, recently, more and more apparatuses are adopting a system (referred to as a consecutive image pickup system) in which, in order to reduce photography time, transmission images of respective projection directions are consecutively photographed while relatively moving the object and the detector.

With a consecutive image pickup system, a positional relationship between a detector and an object changes during exposure. In other words, an object with a motion is to be photographed. Therefore, there is a problem in that a movement blur (referred to as a motion blur) occurs in a transmission image and causes quality of a reconstruction result to decline.

As conventional art devised in consideration with the problem described above, for example, PTL 1 proposes a method which, in a CT apparatus adopting a system which picks up images by having a detector rotate around an object, reduces an effect of a motion blur by measuring MTF characteristics in advance for all angles θ and rotational speeds V at which photography is to be performed and subjecting transmission images to a filtering process using a blur mask filter f (V, θ) created on the basis of the MTF characteristics.

CITATION LIST

Patent Literature

PTL 1: Japanese Patent Application Laid-open No. 2011-194010

SUMMARY OF INVENTION

Technical Problem

A problem in conventional art (the method according to PTL 1) will be described with reference to FIGS. 15A and 15B. FIG. 15A shows a situation where an image pickup system constituted by a light source 150 and a detector 151 takes a photograph while rotating clockwise around an object 152, wherein t0 denotes an exposure start time point and t1 denotes an exposure end time point. In a state (start of exposure) at the time point t0, points P0 to P4 inside the object 152 are all projected to a projection point Q2 on the detector 151. However, projection positions change as the image pickup system rotates and, in a state (end of exposure) at the time point t1, the point P0 is projected to a point Q0, the point P1 is projected to a point Q1, the point P2 is projected to the point Q2, the point P3 is projected to a point Q3, and the point P4 is projected to a point Q4. Such a chancre in projection positions during exposure causes a motion blur to occur during transmission image photography.

Hatched portions in FIG. 15B indicate respective projection ranges (ranges in which projection positions change) of points P0 to P4. Since the projection position of the point P2 that is located at a center of rotation of the image pickup system does not change, a motion blur does not occur. Conversely, at the points P0, P1, P3, and P4 which are located at positions other than the center of rotation, a motion blur occurs due to a change in projection positions on the detector 151. The degree of a motion blur increases with the distance from the point P2 (the center of rotation), and the motion blurs at the points P0 and P1, which are located nearer to the light source than the point P2, are opposite in direction to the motion blurs at the points P3 and P4, which are located nearer to the detector than the point P2. This reveals that the degree and the direction of a motion blur change depending on a position inside the object 152 (this is referred to as "a spatial dependence of motion blur") and that motion blur components of various degrees and directions may be included in a single transmission image.

However, the method according to PTL 1 described above gives no consideration to the spatial dependence of motion blurs and simply uniformly applies, to transmission images, a correction filter f (V, θ) which is determined solely on the basis of a rotational speed V and an angle θ of an image pickup system. With this method, even if a motion blur related to a certain position (for example, the point P1) can be corrected, there is a risk that motion blurs related to other positions (for example, the points P0, P3, and P4) cannot be sufficiently corrected or, even worse, may conversely cause a drop in image quality.

The present invention has been made in consideration of the circumstances described above and aims to provide a technique for suitably correcting a motion blur that is dependent on a position of an object and generating a high-quality reconstructed image from a plurality of transmission images.

Solution to Problem

In order to solve the object described above, an image processing apparatus according to the present invention includes: a transmission image acquiring unit configured to acquire data of a plurality of transmission images obtained by, while relatively moving an image pickup system, the image pickup system being constituted by a light source and a detector, and an object, picking up images of an electromagnetic wave having been transmitted through the object with the detector a plurality of times; and a reconstruction processing unit configured to perform a reconstruction process of generating a reconstructed image of an inside of the object from the plurality of transmission images, wherein the reconstruction processing unit includes a filtering unit which applies, when performing an operation of back-projecting a pixel on the transmission images to a cell on the reconstructed image, a filter for correcting a motion blur attributable to a relative movement of the image pickup system and the object to the transmission images, and wherein a filter that the filtering unit uses when a pixel on a first transmission image is back-projected to a first cell on the reconstructed image is different from a filter that the filtering unit uses when the pixel on the first transmission image is back-projected to a second cell existing at coordinates that differ from those of the first cell.

According to this configuration, in a back projection operation, a filter used for motion blur correction can be appropriately changed depending on coordinates of a cell on the reconstructed image to which a pixel on a transmission image is back-projected. Therefore, blur correction taking into consideration a spatial dependence of a motion blur (differences in degrees and directions of a motion blur for each cell of the reconstructed image or, in other words, for each position inside the object) can be achieved, and, as a result, quality of the reconstructed image can be improved.

A filter that the filtering unit uses when a pixel on the first transmission image is back-projected to the first cell may be different from a filter that the filtering unit uses when a pixel on a second transmission image that differs from the first transmission image is back-projected to the first cell. According to this configuration, even when image pickup conditions (conditions related to a relative positional relationship and a relative movement between the image pickup system and the object) differ between when the first transmission image is picked up and when the second transmission image is picked up, an appropriate filter in accordance with each transmission image can be applied.

More specifically, the plurality of transmission images are picked up by changing image pickup conditions which are conditions related to a relative positional relationship and a relative movement between the image pickup system and the object, and the filtering unit may switch filters to be used in accordance with a combination of the image pickup conditions of a transmission image and coordinates of a cell that is a back projection destination.

The image processing apparatus may include a storage unit which stores a plurality of filters associated with combinations of image pickup conditions and coordinates of cells, and the filtering unit may acquire a filter to be applied to a transmission image from the storage unit on the basis of image pickup conditions of the transmission image and coordinates of a cell that is a back projection destination. According to this configuration, since there is no longer a need to recalculate a filter during a reconstruction process, a faster reconstruction process can be achieved.

The reconstruction process may be a process using a filtered back projection method. A reconstruction process using the filtered back projection method has an advantage in that a relatively high-quality reconstruction result can be computed at high speed. The present invention can also be applied to reconstruction algorithms other than the filtered back projection method as long as the algorithms require back projection.

The present invention can be considered an image processing apparatus including at least a part of the components or functions described above. In addition, the present invention can also be considered a CT apparatus provided with an image processing apparatus and an inspection apparatus or a diagnostic apparatus utilizing reconstructed three-dimensional images. Furthermore, the present invention can also be considered an image processing method, a CT apparatus control method, an inspection method, and a diagnostic method which include at least apart of the processes described above, a program causing a computer to execute the methods, or a computer-readable recording medium which records such a program on a non-transitory basis. The respective components and processes described above can be combined with one another in any way possible to constitute the present invention insofar as technical contradictions do not arise.

Advantageous Effects of Invention

According to the present invention, a high-quality reconstructed image can be generated at high speed from a plurality of transmission images.

BRIEF DESCRIPTION OF DRAWINGS

FIG. 3 is a block diagram showing a configuration of an image processing apparatus.

FIG. 5 is a diagram showing a reconstruction process according to a simple back projection method.

FIG. 8 is a diagram showing an example of image pickup conditions.

FIG. 9 is an example of data tables of motion blurs and motion blur correction filters.

FIGS. 15A and 15B are diagrams for explaining a problem of motion blur in consecutive image pickup.

DESCRIPTION OF EMBODIMENTS

Hereinafter, a preferred embodiment of the present invention will be described with reference to the drawings. However, it is to be understood that the description of the respective components presented below are intended to be changed as deemed appropriate in accordance with configurations and various conditions of systems to which the present invention is to be applied and are not intended to limit the scope of the invention to the description presented below.

(System Configuration)

Figure 1:
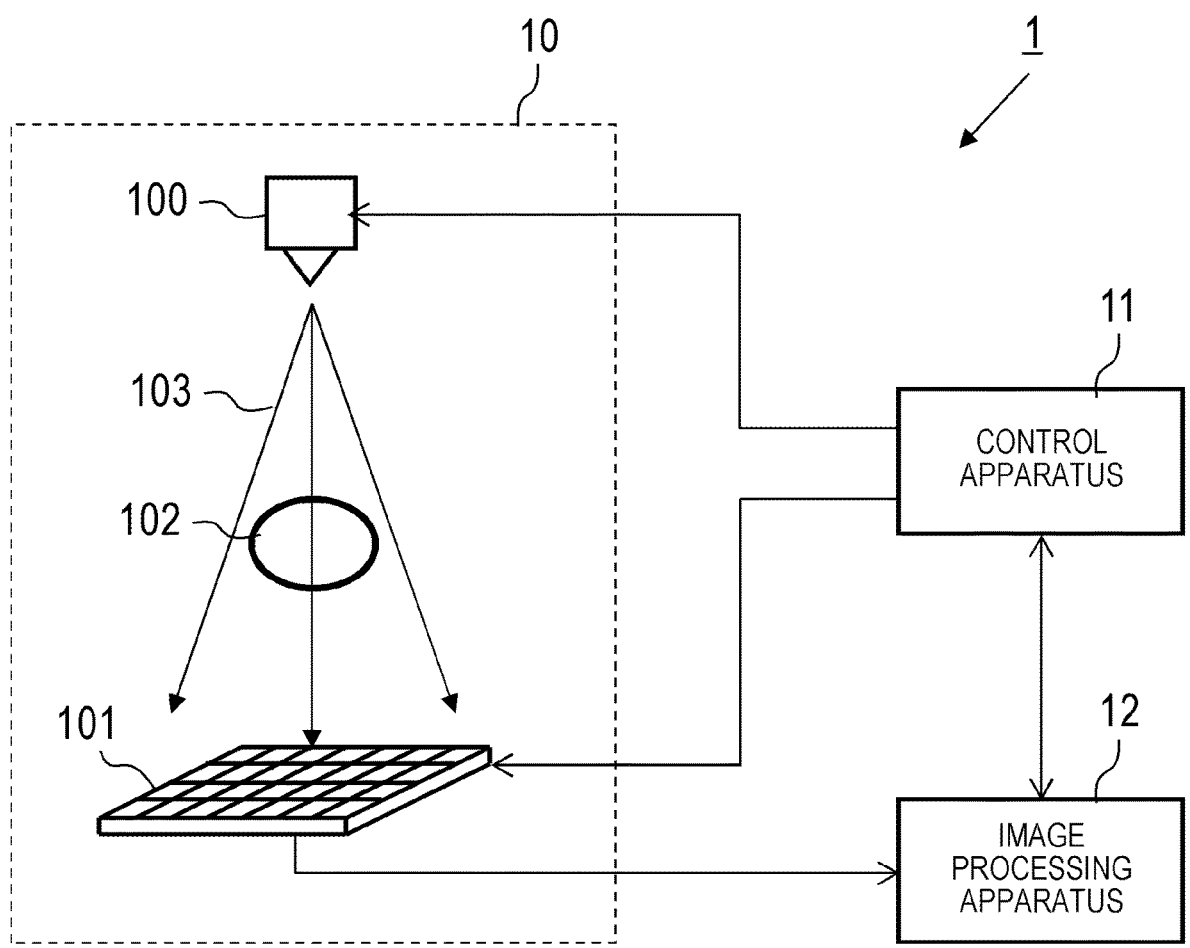
FIG. 1 is a diagram schematically showing a hardware configuration of a CT system according to an embodiment of the present invention.

FIG. 1 schematically shows a hardware configuration of a CT system 1 according to an embodiment of the present invention. The CT system 1 is a system which acquires data of a three-dimensional image or a tomographic image of an inside of an object 102 using a CT (Computed Tomography) technique. For example, the CT system 1 can be applied to a medical examination apparatus which visualizes an inside of a human being or an animal to perform a diagnosis or an examination and to an industrial inspection apparatus which performs non-destructive testing of an internal structure of an industrial product.

The CT system 1 is generally configured so as to include an image pickup apparatus 10, a control apparatus, and an image processing apparatus 12. The image pickup apparatus 10 is an apparatus which picks up a transmission image of the object 102. The control apparatus 11 is an apparatus which controls operations of respective units of the image pickup apparatus 10. The image processing apparatus 12 is an apparatus which subjects data (also referred to as projection data) of a transmission image acquired by the image pickup apparatus 10 to image processing and arithmetic processing. The image pickup apparatus 10, the control apparatus 11, and the image processing apparatus 12 may be constituted by an integrated apparatus or respectively constituted by separate apparatuses.

The image pickup apparatus 10 has an image pickup system constituted by a light source 100 and a detector 101 arranged so as to oppose each other. A transmission image of the object 102 is obtained by having the light source 100 project an electromagnetic wave 103 with respect to the object 102 and having the detector 101 pick up the electromagnetic wave 103 transmitted through the object 102. For example, a configuration may be adopted in which a cone beam X-ray source is used as the light source 100, a two-dimensional X-ray detector constituted by a scintillator and a two-dimensional CMOS sensor is used as the detector 101, and a two-dimensional X-ray transmission image of the object 102 is obtained by one image pickup operation. Alternatively, a fan beam-type light source or a parallel beam-type light source may be used as the light source 100. In addition, besides X-rays, an electromagnetic wave (such as a gamma ray or visible light) having certain transmittivity with respect to the object 102 may be used for image pickup operations.

Figure 2C:
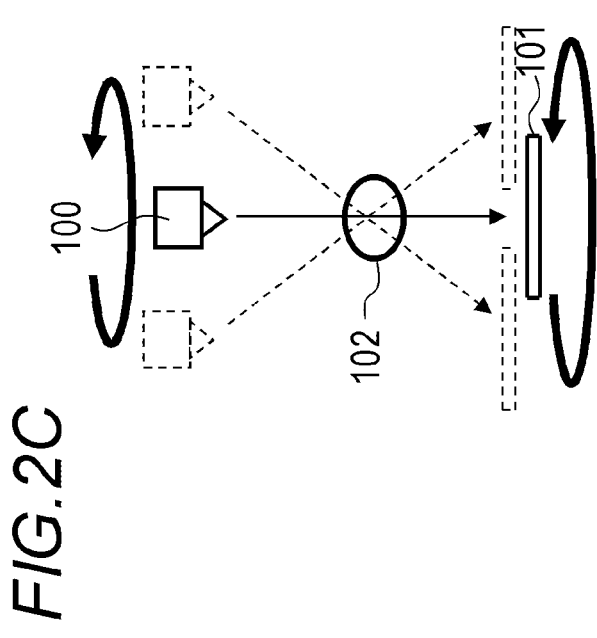
FIGS. 2A to 2D are diagrams showing an example of a movement system of a light source, an object, and a detector.
Figure 2D:
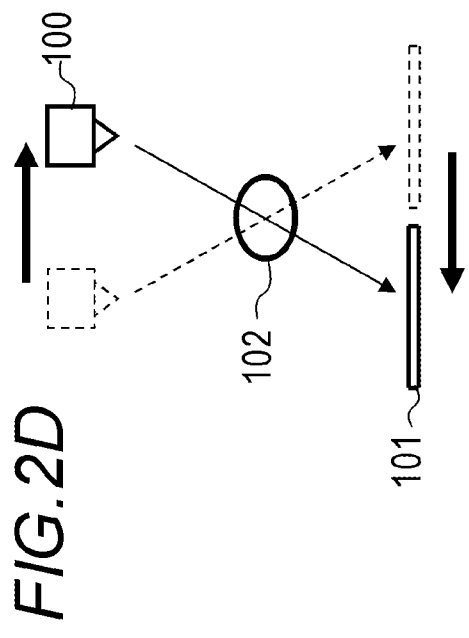
Figure 2A:
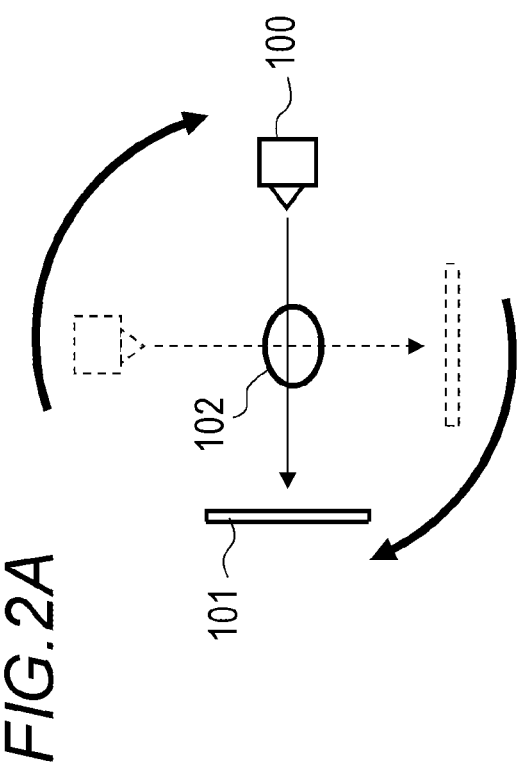
Figure 2B:
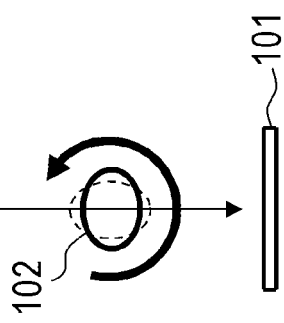

In addition, the image pickup apparatus 10 includes a moving mechanism (not illustrated) for changing a relative positional relationship (a projection direction of an electromagnetic wave with respect to the object 102) and a relative movement (a movement speed and a movement direction) between the image pickup system (the light source 100 and the detector 101) and the object 102. Examples of a configuration of the moving mechanism include various systems such as a type in which the light source 100 and the detector 101 revolve around the object 102 being fixed as shown in FIG. 2A, a type in which the object 102 rotates in place while the light source 100 and the detector 101 are fixed as shown in FIG. 2B, a type in which the light source 100 and the detector 101 respectively gyrate within a plane perpendicular to an axis that passes through the object 102 as shown in FIG. 2C, and a type in which the object 102 is fixed while the light source 100 and the detector 101 move parallel to and in opposite directions to each other as shown in FIG. 2D.

The control apparatus 11 is an apparatus which performs overall control of the CT system 1 such as projection and suspension of the light source 100, image pickup operations using the detector 101, and changing projection directions (driving of the moving mechanism).

The image processing apparatus 12 is an apparatus which performs image processing and arithmetic processing on data of transmission images acquired by the image pickup apparatus 10. In accordance with an object and an application of the image processing apparatus 12, various processes can be implemented in the image processing apparatus 12 including a reconstruction process of generating a reconstructed image (also referred to as a three-dimensional image or volume data) of the object 102 from data of a plurality of transmission images picked up from different projection directions, a process of generating an arbitrary tomographic image from a reconstructed image, and a process of extracting a feature amount or performing an examination or a diagnosis using data of a reconstructed image or a tomographic image.

The image processing apparatus 12 can be constituted by a computer provided with a processor (CPU), a memory, a storage apparatus (such as a hard disk drive), an input apparatus (such as a mouse, a keyboard, or a touch panel), and an output apparatus (such as a display apparatus). Functions of the image processing apparatus 12 to be described later are realized as the processor executes a program stored in the storage apparatus. Alternatively, a part of or all of the functions of the image processing apparatus 12 may be constituted by an ASIC, an FPGA, or the like. Alternatively, a part of or all of the functions of the image processing apparatus 12 may be executed by another computer, a server on a network, or the like.

FIG. 3 is a block diagram showing a configuration of the image processing apparatus 12. The image processing apparatus 12 includes a transmission image acquiring unit 30, a reconstruction processing unit 31, a parameter storage unit 32, and a filter generating unit 33. In addition, the reconstruction processing unit 31 includes a filtering unit 34.

The transmission image acquiring unit 30 has a function of acquiring data (in other words, original data to be used for reconstruction) of a plurality of transmission images with different projection directions. The transmission image acquiring unit 30 may directly acquire data of the transmission images from the image pickup apparatus 10 or may load data of previously picked-up transmission images from a storage apparatus or an external data storage. The reconstruction processing unit 31 has a function of performing a reconstruction process of generating a reconstructed image of the inside of the object 102 from a plurality of transmission images. As an algorithm of the reconstruction process, any of algorithms including a simple back projection method, a filtered back projection method, a SIRT (simultaneous reconstruction technique) method, an ART (algebraic reconstruction technique) method, a search method (gradient method), a conjugate gradient method, and a steepest descent method may be used. In the present embodiment, the filtered back projection method which has an advantage in that a relatively high-quality reconstruction result can be computed at high speed is used. The parameter storage unit 32 has a function of storing various parameters (set values, definition data, tables, filters, and the like) used in the reconstruction process. The filter generating unit 33 has a function of generating a filter for motion blur correction. The filtering unit 34 has a function of applying a filter for motion blur correction filter to a transmission image.

(Principles of Image Pickup and Reconstruction)

Figure 4A:
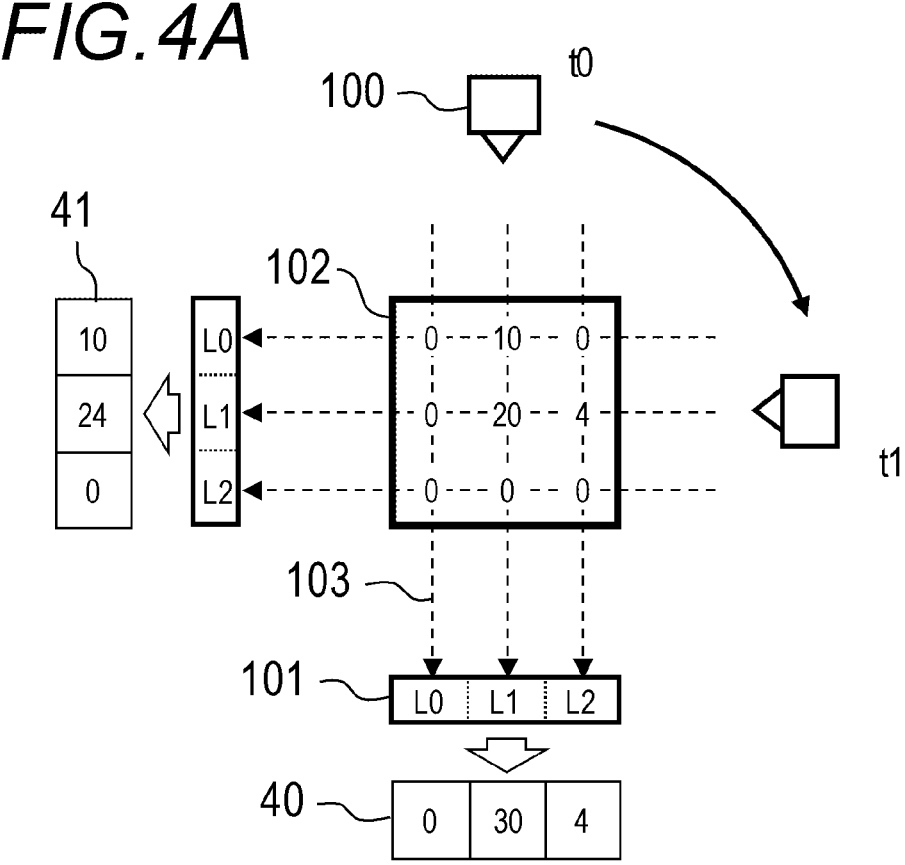
FIG. 4A is a diagram showing a basic principle of image pickup.
Figure 4B:
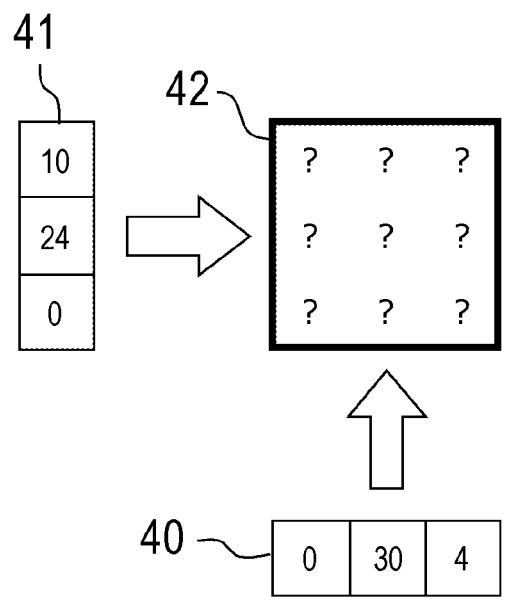
FIG. 4B is a diagram showing a reconstruction process.

Before describing features of the present embodiment, basic principles of image pickup and reconstruction in a general CT apparatus will be described with reference to FIGS. 4A and 4B. For the sake of brevity, FIG. 4A shows an example in which photography of a one-dimensional transmission image is performed twice using a parallel beam and the detector 101 having three pixels L0 to L1. Although an actual apparatus picks up two-dimensional transmission images using a cone beam and the number of transmission images (the number of projections) ranges from several ten to several hundred and the number of pixels of the transmission images ranges from several ten thousand to several million, a basic principle similar to that shown in FIG. 4A.

In FIG. 4A, numerical values indicated inside the object 102 represent an X-ray attenuation coefficient distribution and dash line arrows indicate transmission paths (projection lines) of an X-ray 103. First, at a time point t0, the light source 100 and the detector 101 are arranged above and below the object 102, the X-ray 103 is projected from the light source 100, and a first transmission image 40 is photographed by the detector 101. A part of energy of the X-ray 103 is absorbed when being transmitted through the object 102 and the X-ray 103 attenuates. Normally, since the X-ray attenuation coefficient distribution inside the object 102 is not uniform, a difference in attenuation rates of the X-ray 103 is created depending on a transmission path (a natural logarithm of the attenuation rate of the X-ray 103 from which a negative sign is removed corresponds to an integrated value of X-ray attenuation coefficients on a transmission path). However, a value of the transmission image 40 is obtained by dividing an observed value of the object 102 by an observed value when the object 102 does not exist, taking a natural logarithm of the value, and removing a negative sign thereof.

At a time point t1, the light source 100 and the detector 101 are moved and, after changing a protection direction clockwise by 90 degrees, the X-ray 103 is projected from the light source 100 to photograph a second transmission image 41. Since the transmission path of the X-ray 103 are different between the first transmission image 40 and the second transmission image 41, it is obvious that different values are to be observed.

After obtaining the plurality of transmission images 40 and 41 with different projection directions as described above, a reconstruction process is performed using the transmission images 40 and 41. As shown in FIG. 4B, the reconstruction process corresponds to a process of estimating an X-ray attenuation coefficient distribution 42 inside the object 102 on the basis of the plurality of transmission images 40 and 41.

FIG. 5 schematically shows a reconstruction process according to a simple back projection method. First, a data region of a reconstructed image 50 corresponding to one section of the object 102 is secured on a memory and each cell is initialized by zero. Then, the transmission image 40 is back-projected on the reconstructed image 50. Back projection refers to an operation of projecting a point on the transmission image 40 to a point on the reconstructed image 50 and, in this case, back projection is equivalent to a process of writing (adding) a value of a pixel on the transmission image 40 to a corresponding cell on the reconstructed image 50. The corresponding cell is a pixel existing on a transmission path of the X-ray and, in the example shown in FIG. 5, three corresponding cells exist for each pixel of the transmission image 40. The same value is written (added) to the three corresponding cells. Subsequently, the transmission image 41 is back-projected on the reconstructed image 50 in a similar manner. The reconstructed image 50 can be obtained by performing this process on all of the transmission images and accumulatively adding the back projections of all of the transmission images. In FIG. 5, a result of the accumulative addition of the back projections is subsequently divided by the number of projections (in this case, 2). This concludes the summary of the reconstruction process according to a simple back projection method. A feature of the filtered back projection method used in the present embodiment is that a transmission image is back-projected after being subjected to a high-pass filter, and other operations are basically the same as those of the simple back projection method.

(Consecutive Image Pickup System and Problems Thereof)

The image pickup apparatus 10 according to the present embodiment uses a system (a consecutive image pickup system) which consecutively photographs transmission images of respective projection directions while relatively moving an image pickup system and the object 102. This is because the consecutive image pickup system is capable of improving throughput as compared to a so-called Stop & Go system in which images are picked after stopping the relative movement of the image pickup system and the object 102. However, as described with reference to FIGS. 15A and 15B, with the consecutive image pickup system, a change in projection positions during exposure creates a blur referred to as a motion blur. In addition, since the degree and the direction of a motion blur differ depending on a position inside the object 102, a single transmission image ends up containing blur components with various degrees and directions.

In consideration thereof, in the present embodiment, when performing an operation of back-projecting a pixel on a transmission image to a cell on a reconstructed image in the reconstruction process, a motion blur correction filter is applied to the transmission image and a pixel value after filtering is back-projected to the cell. At this point, blur correction which takes a spatial dependence of a motion blur into consideration is realized by switching filters to be applied to the transmission image in accordance with coordinates of the cell that is a back projection destination. Hereinafter, a filter generating process and the reconstruction process according to the present embodiment will be described in detail.

(Filter Generating Process)

Figure 6:
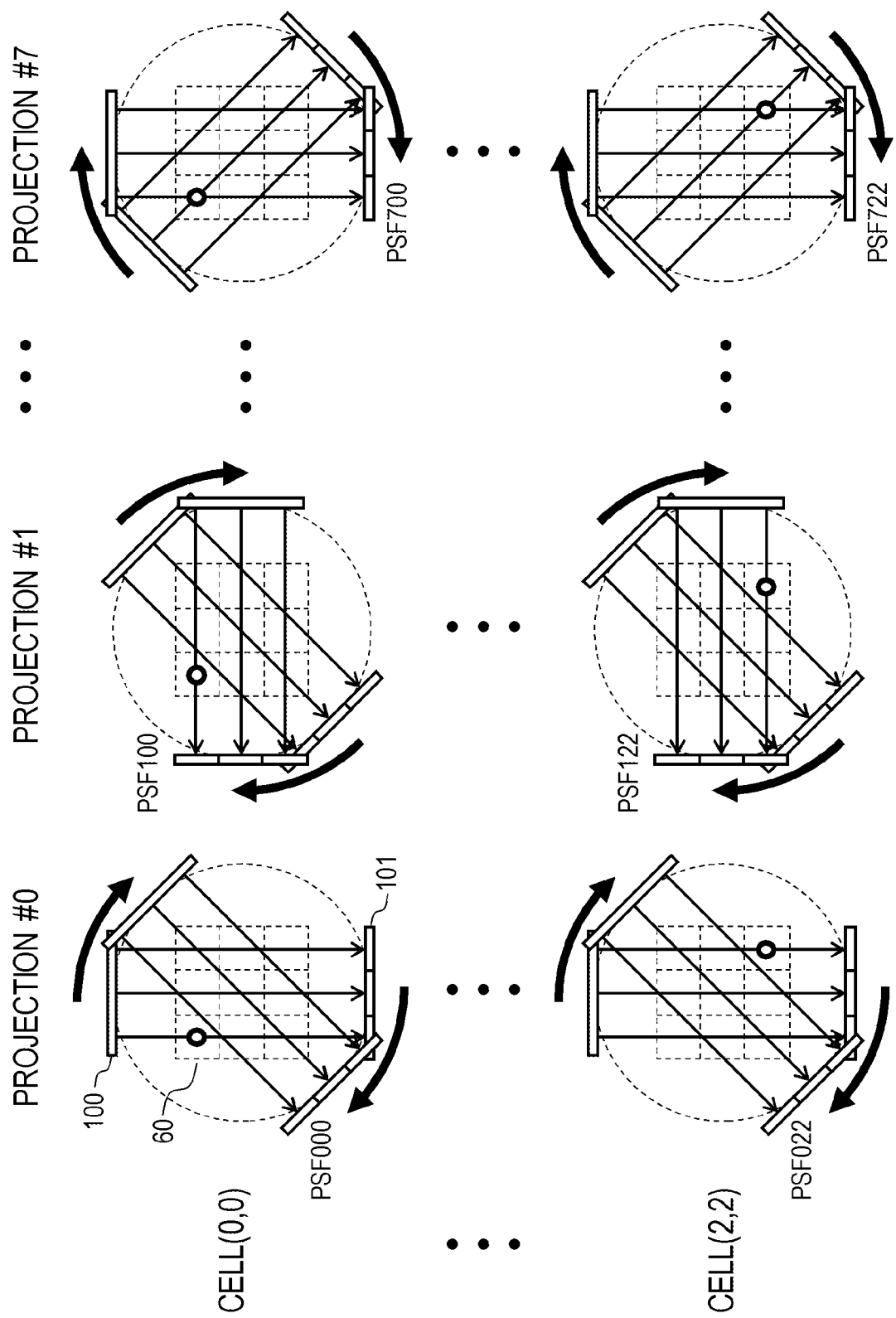
FIG. 6 is a diagram showing a model used in a generation process of a motion blur correction filter.
Figure 7:
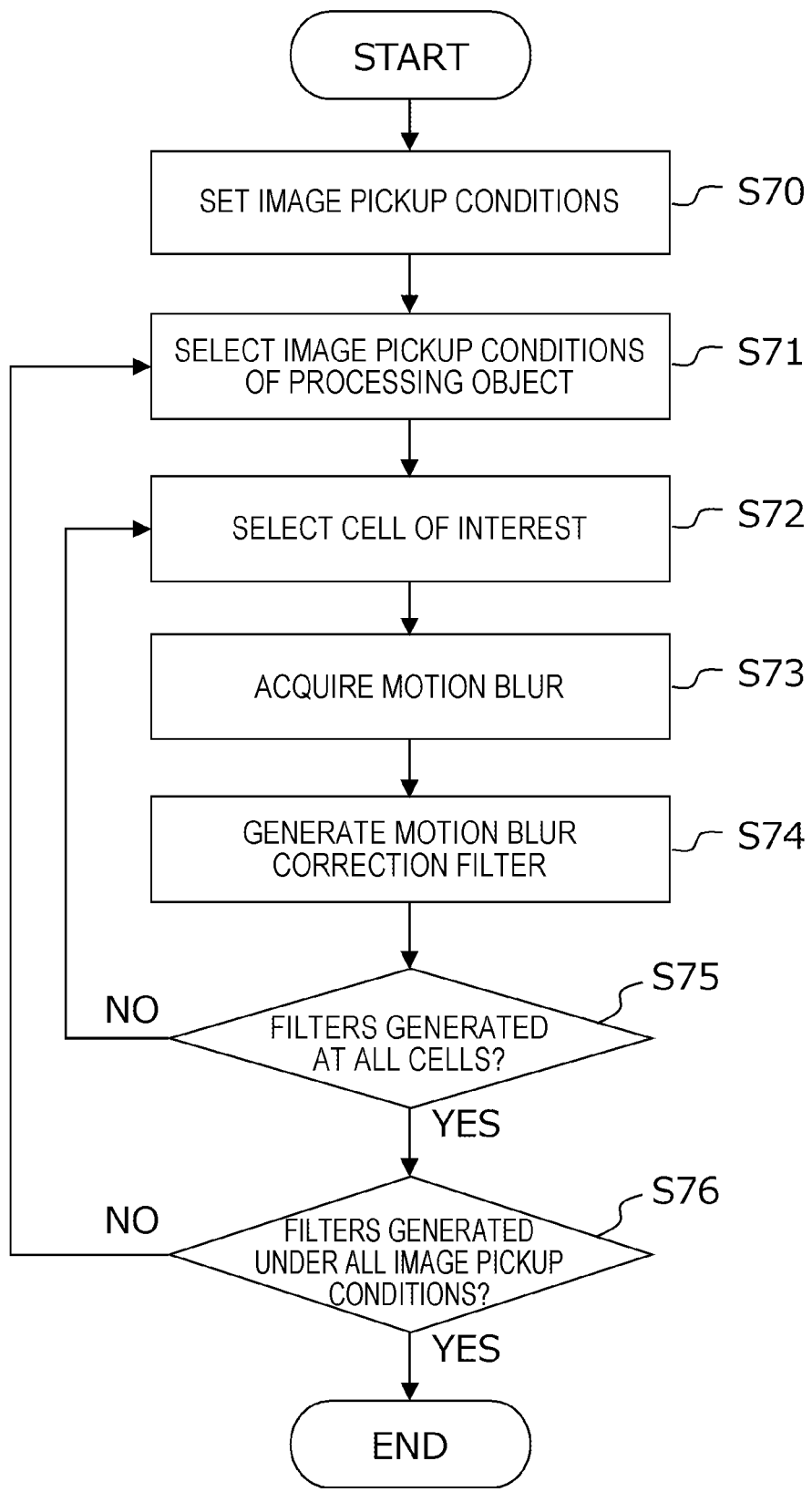
FIG. 7 is a flow chart of a generation process of a motion blur correction filter.

FIGS. 6 and 7 show a generation process of a motion blur correction filter.

In this case, for the sake of brevity, a model is assumed in which a reconstructed image with 3×3 cells is generated using an image pickup system constituted by a parallel beam light source 100 and a one-dimensional detector 101 with 1×3 cells. Although an actual apparatus picks up two-dimensional transmission images using a cone beam and sizes of transmission images and reconstructed images equal or exceed several ten thousand pixels, a basic concept is similar to a method described below. In FIG. 6, a reference numeral 60 virtually indicates a position of each cell of a reconstructed image. In a coordinate system of the reconstructed image 60, an x axis is oriented rightward and a y axis is oriented downward in FIG. 6, coordinates of a top left cell of the reconstructed image 60 is expressed as (x, y)=(0, 0), and coordinates of a bottom right cell of the reconstructed image 60 is expressed as (x, y)=(2, 2).

First, in step S70 in FIG. 7, image pickup conditions when picking up each transmission image are set. Image pickup conditions refer to conditions that define a relative positional relationship and a relative movement between the image pickup system (the light source 100 and the detector 101) and an object when photographing a transmission image. In the case of a configuration shown in FIG. 6, for example, rotation angles of the image pickup system upon start of exposure and end of exposure (during data capture) and the like are set as conditions related to the relative positional relationship, and a rotational speed (angular velocity), a rotation direction (clockwise or counterclockwise), and the like of the image pickup system are set as conditions related to the relative movement. FIG. 8 represents a setting example of image pickup conditions in a case where images are picked up eight times (referred to as projection #0 to projection #7) during $2\pi$ [rad] while rotating the image pickup system clockwise at a constant angular velocity v.

Next, an acquisition process of a motion blur is performed. As described earlier, the degree and the direction of a motion blur are not only dependent on image pickup conditions (the relative positional relationship and the relative movement of the image pickup system and the object) but are also dependent on a position inside the object. Therefore, in the present embodiment, with respect to each image pickup condition, a motion blur is individually acquired for each position inside the object (in other words, for each cell of the reconstructed image 60 shown in FIG. 6).

Specifically, the filter generating unit 33 selects an image pickup condition (for example, projection #0) to be a processing object (step S71) and selects a cell of interest (for example, (0, 0)) (step S72). In addition, the filter generating unit 33 acquires a motion blur that is observed by the detector 101 when an object existing at the cell of interest (0, 0) is picked up under the image pickup condition of projection #0 (step S73). In this case, an image observed by the detector 101 when a point target is installed at the cell of interest or, in other words, a point spread function (PSF) is used as a motion blur. Alternatively, a motion blur (PSF) may be acquired by actually measuring a point target installed at a position of the cell of interest or may be geometrically calculated on the basis of conditions of the relative positional relationship and the relative movement between the image pickup system and the cell of interest. Accordingly, a motion blur PSF000 corresponding to a combination of projection #0 and the cell of interest (0, 0) can be acquired. In the suffix "000", a first numeral indicates a number of the image pickup condition while second and third numerals indicate an x coordinate and a y coordinate of the cell.

Next, the filter generating unit 33 generates a motion blur correction filter using the motion blur acquired in step S73 (step S74). As the motion blur correction filter, any image restoration filter having a blur reduction effect may be used. For example, a Wiener Filter or a Rucy-Richardson method may be favorably used.

As an example, a generation procedure of a Wiener Filter will be described. The filter generating unit 33 performs a Fourier transform of the motion blur PSF acquired in step S73 and obtains an MTF (Modulation Transfer Function). FT { } in the following equation represents a Fourier transform.

$$MTF=FT\{PSF\}$$

Subsequently, the filter generating unit 33 generates a Wiener Filter H of a frequency region using the following equation.

$$H=MTF^*/(|MTF|^2+NSR),$$

where * represents complex conjugation and NSR denotes a constant.

A Wiener Filter h of a spatial region is obtained by performing an inverse Fourier transform on the filter H of the frequency space. IFT { } in the following equation represents an inverse Fourier transform.

$$h=IFT\{H\}$$

According to the processes described above, a motion blur correction filter h000 corresponding to the combination of projection #0 and the cell of interest (0, 0) can be acquired.

By executing the processes of steps S72 to S74 with respect to all cells (0, 0), (1, 0), (2, 0), (0, 1), (1, 1), (2, 1), (0, 2), (1, 2), and (2, 2) (step S75), motion blurs PSF000, PSF010, PSF020, PSF001, PSF011, PSF021, PSF002, PSF012, and PSF022 and filters h000, h010, h020, h001, h011, h021, h002, h012, h022 corresponding to the respective cells when images are picked up under the image pickup condition of projection #0 can be acquired. Once the processes of steps S71 to S75 are executed with respect to all image pickup conditions (projection #0 to projection #7) (step S76), the filter generating unit is ended.

FIG. 9 shows examples of a data table of acquired motion blurs and a data table of motion blur correction filters generated from the acquired motion blurs. The data table of the motion blur correction filters is stored in the parameter storage unit 32 of the image processing apparatus 12 to be used in a reconstruction process to be described later.

While a motion blur correction filter is individually prepared for all combinations of an image pickup condition and a cell in the present embodiment, a plurality of cells of which motion blurs have the same or similar degrees and directions may share an identical filter. Accordingly, the filter generating process can be sped up and a storage capacity of the parameter storage unit 32 can be reduced.

(Image Pickup)

Figure 10:
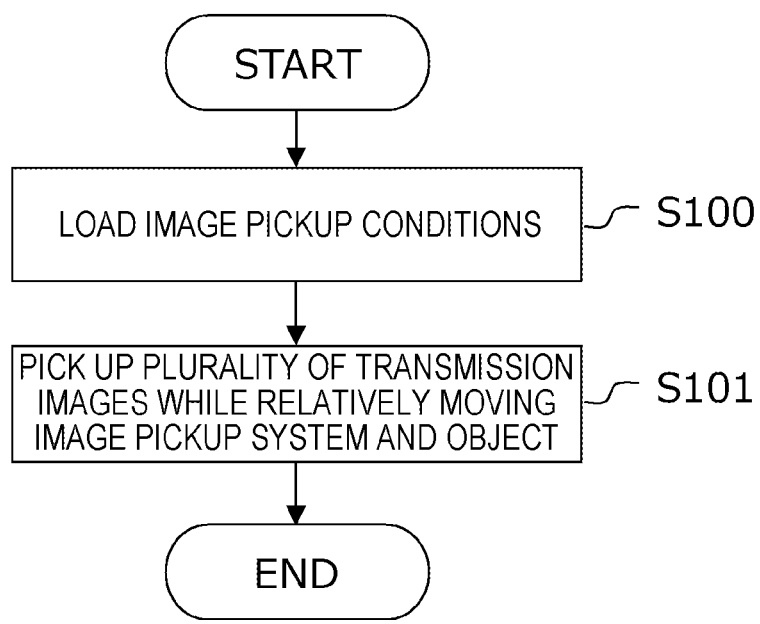
FIG. 10 is a flow chart of consecutive image pickup.
Figure 11:
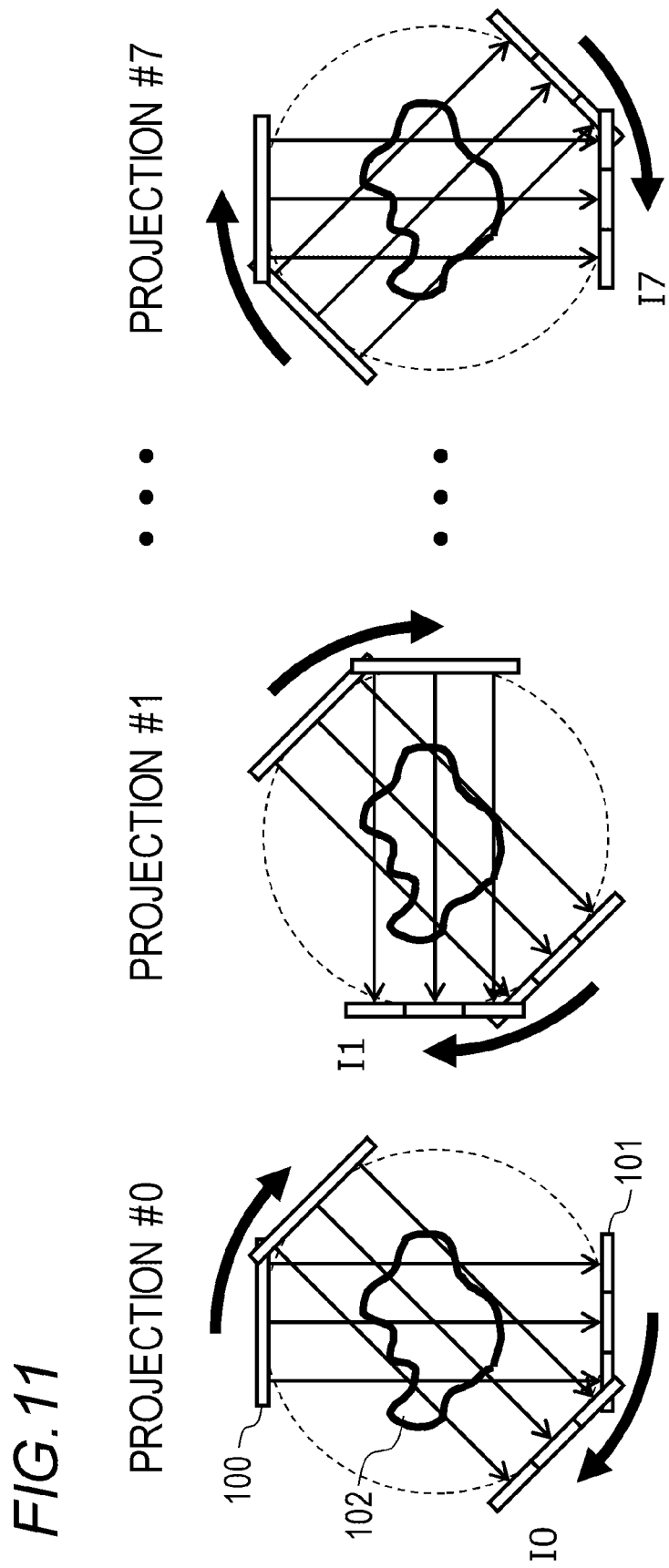
FIG. 11 is a diagram showing how consecutive image pickup is performed.

FIGS. 10 and 11 show a procedure of consecutive image pickup by the image pickup apparatus 10.

In step S100, image pickup conditions set in advance are loaded to the control apparatus 11. In this case, it is assumed that respective image pickup conditions of projection #0 to projection #7 shown in FIG. 8 are loaded. In addition, due to the control apparatus 11 controlling movement, exposure, and image pickup by the image pickup apparatus 10 in accordance with the image pickup conditions, as shown in FIG. 11, pickup of seven transmission images I0 to I7 are consecutively executed while rotating the image pickup system (step S101). Data of the transmission images I0 to I7 acquired by the image pickup apparatus 10 is sent to the image processing apparatus 12.

(Reconstruction Process)

Figure 12:
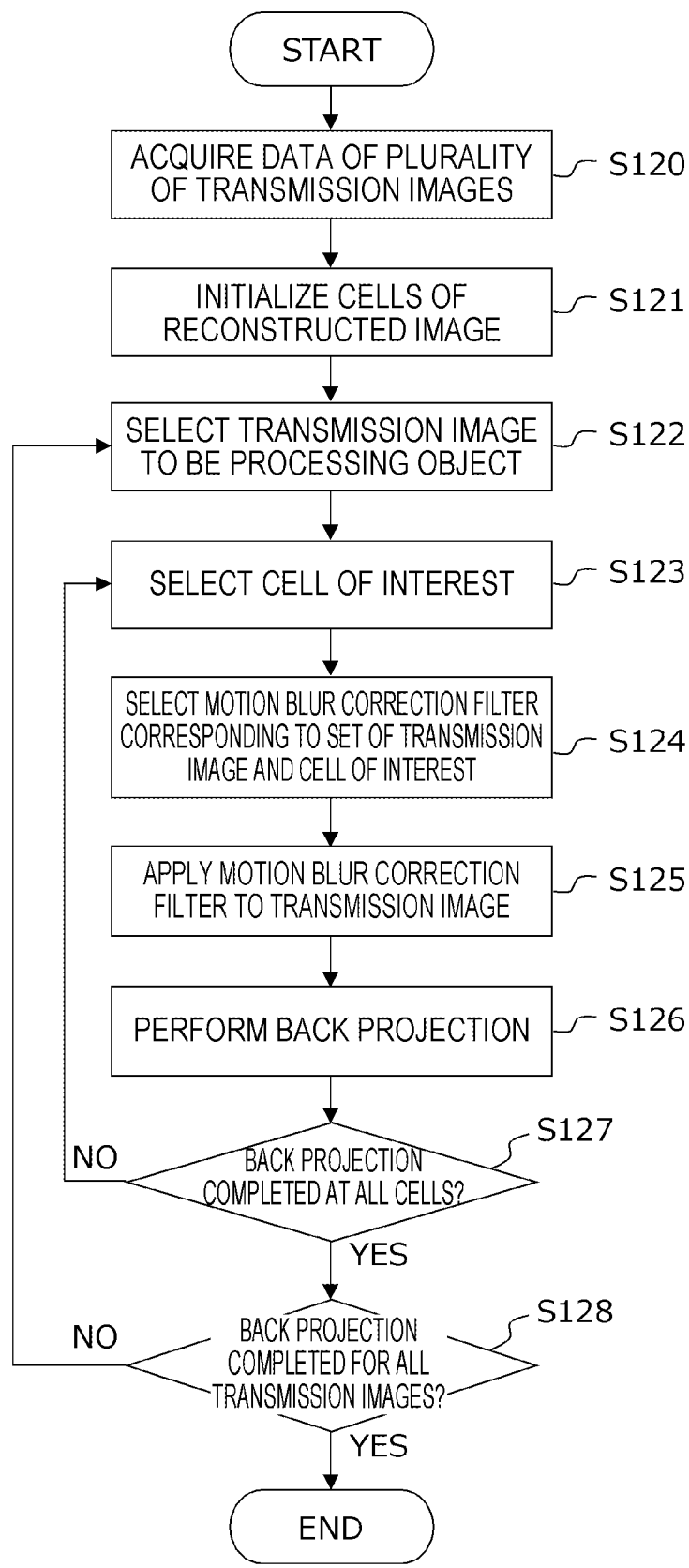
FIG. 12 is a flow chart of a reconstruction process.

FIG. 12 shows a procedure of a reconstruction process in the image processing apparatus 12. A feature of the reconstruction process according to the present embodiment is that a motion blur correction filter to be applied to a transmission image is switched in accordance with a combination of an image pickup condition of the transmission image and coordinates of a cell that is a back projection destination.

First, in step S120, the transmission image acquiring unit 30 acquires data of the transmission images I0 to I7 from the image pickup apparatus 10. The pieces of data are stored in a memory or a storage apparatus to be used in the subsequent reconstruction process. In step S121, the reconstruction processing unit 31 secures a data region of the reconstructed image 60 on the memory and initializes each cell by zero.

Next, the reconstruction processing unit 31 selects a transmission image (for example, the transmission image I0) to be a processing object (step S122) and, at the same time, selects a cell of interest (for example, (0, 0)) of the reconstructed image 60 to be a back projection destination (step S123). In addition, the filtering unit 34 acquires a motion blur correction filter (h000) corresponding to the combination of the image pickup condition (projection #0) of the transmission image (I0)) and the cell of interest (0, 0) from the parameter storage unit 32 (step S124), and applies the motion blur correction filter (h000) to the transmission image (I0) (step S125). Accordingly, a motion blur of an image of an object existing in the cell of interest (0, 0) is reduced. Next, the reconstruction processing unit 31 applies a high-pass filter to the transmission image (I0) after the motion blur correction and, after performing necessary normalization (division by the number of projections), adds a pixel of the transmission image (I0) to the cell of interest (0, 0) of the reconstructed image 60 (step S126). This concludes the description of an operation of a back projection of the transmission image (ID) obtained under the image pickup condition (projection #0) with respect to the cell of interest (0, 0).

By executing the processes of steps S123 to S126 with respect to all of the cells (0, 0), (1, 0), (2, 0), (0, 1), (1, 1), (2, 1), (0, 2), (1, 2), and (2, 2) (step S127), back projection of the transmission image I0 picked up under the image pickup condition of projection #0 is completed. Furthermore, by further performing the processes of steps S122 to S127 on the transmission images I0 to I7 in sequence (step S128) and accumulatively adding the back projections of all of the transmission images I0 to I7, a reconstructed image can be obtained.

Figure 13:
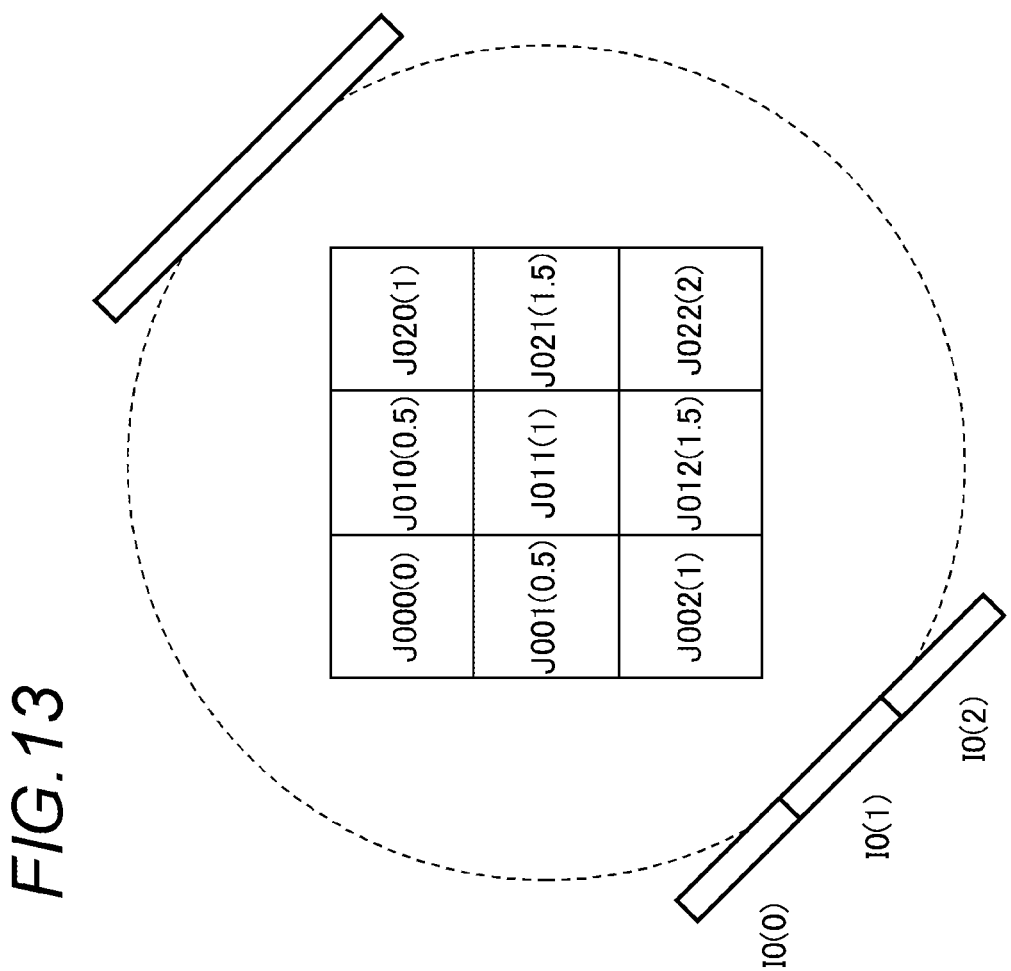
FIG. 13 is a diagram showing operations of filtering for motion blur correction and back projection.

FIG. 13 schematically shows operations of filtering for motion blur correction and back projection. In FIG. 13, $h_{HPF}$ denotes a high-pass filter, a symbol of operation drawn as a circled X represents a convolution operation, and J denotes a result obtained by applying a motion blur correction filter h and a high-pass filter $h_{HPF}$ to a transmission image I and performing normalization (division by 8 (the number of projections)). In the three-digit suffixes of J and h, a first numeral indicates a number of the image pickup condition while second and third numerals indicate an x coordinate and a y coordinate of the cell. In addition, bracketed indexes added to I and J indicate coordinates of a pixel. With respect to results of which the index is not an integer such as J010 (0.5), a value is obtained by a linear interpolation of neighboring pixels (for example, J010 (0.5)={J010 (0)+J010 (1)}/2).

As shown in FIG. 13, in the present embodiment, a motion blur correction filter to be applied to a transmission image is switched in accordance with a combination of an image pickup condition of the transmission image and coordinates of a cell that is a back projection destination. Accordingly, blur correction that takes a spatial dependence of a motion blur into consideration can be realized and quality of a final reconstruction result can be improved.

As is apparent from FIG. 13, only a part of the pixels of a transmission image is used for back projection. Therefore, an amount of arithmetic operations may be reduced by limiting a range in which operations of a motion blur correction filter and a high-pass filter are performed to a section (only a range necessary for back projection) of a transmission image. Alternatively, the amount of arithmetic operations may be reduced by performing operations of a motion blur correction filter and a high-pass filter only on discretely selected partial cells and obtaining values with respect to other cells by interpolation. For example, by performing filter operations of J000 and J020 and obtaining a value of J010 by a linear interpolation of a value of J000 and a value of J020, the number of filter operations can be reduced to ⅔.

According to the configuration of the present embodiment described above, in a back projection operation, a filter used for motion blur correction can be appropriately changed depending on coordinates (in other words, a position inside an object) of a cell that is a back projection destination. Therefore, blur correction can be performed which takes into consideration a spatial dependence of motion blur (differences in degrees and directions of motion blur among cells of the reconstructed image or, in other words, among positions in the object) and, as a result, quality of the reconstructed image can be improved. In addition, even when image pickup conditions (a relative positional relationship between the image pickup system and the object, a speed and a direction of relative movement, and the like) of transmission images differ, an appropriate filter in accordance with each image pickup condition can be applied. Furthermore, according to the present embodiment, since a motion blur correction filter is calculated in advance and stored in the parameter storage unit 32, there is no longer a need to recalculate a filter during a reconstruction process and a faster reconstruction process can be achieved.

EXAMPLE

Figure 14A:
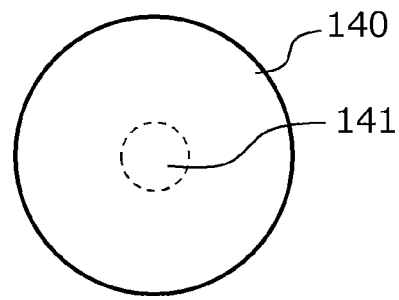
FIGS. 14A to 14G are diagrams showing an effect verification result by computer simulation.
Figure 14B:
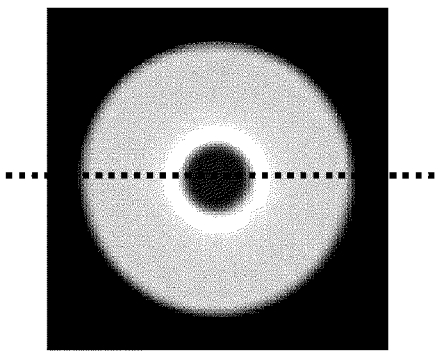
Figure 14E:
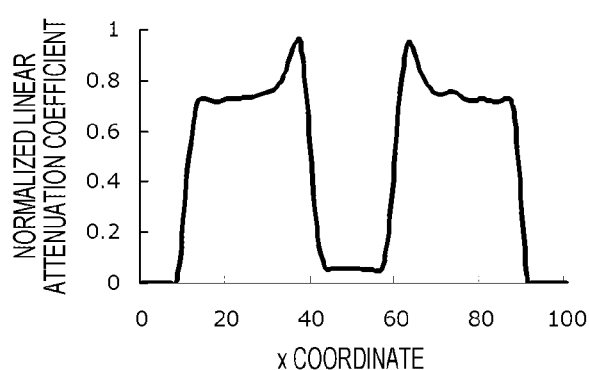
Figure 14C:
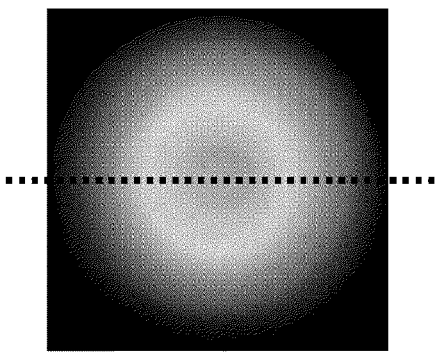
Figure 14F:
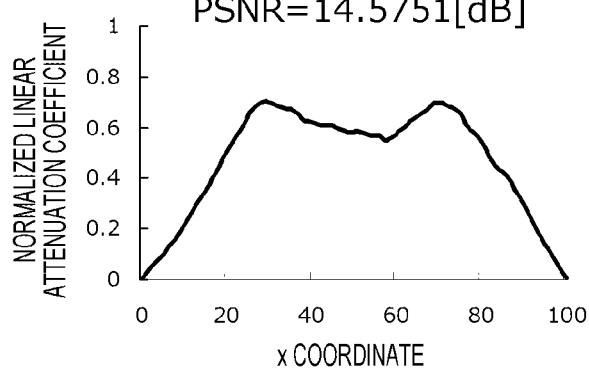
Figure 14D:
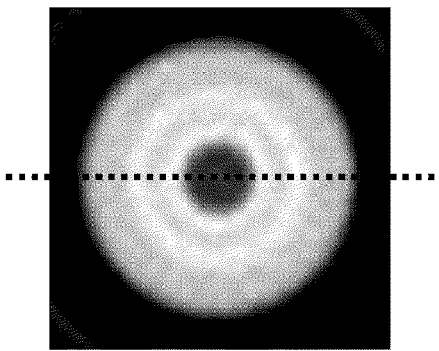

FIGS. 14A to 14G show an effect verification result by computer simulation. FIG. 14A shows a model of an object. In this case, a model 140 that is a spherical body having an internal cavity 141 is used. FIGS. 14B, 14C, and 14D show results obtained by generating X-ray transmission images in 32 directions with respect to the model 140 by simulation, performing a CT reconstruction of the 32 transmission images, and slicing a reconstructed image (three-dimensional image) at a center of the spherical body. FIG. 14B shows a reconstruction result using a transmission image according to a Stop & Go system (still image pickup system) or, in other words, a transmission image without a motion blur. FIGS. 14C and 14D show reconstruction results using a transmission image according to a consecutive image pickup system or, in other words, a transmission image including a motion blur, in which FIG. 14C shows an example of performing a back projection without performing motion blur correction and FIG. 14D shows an example of performing the motion blur correction according to the present embodiment. In addition, FIGS. 14E to 14G respectively show profiles at dash line positions in FIGS. 14B to 14D, in which an abscissa represents an x coordinate of an image and an ordinate represents a normalized linear attenuation coefficient.

PSNR (peak signal-to-noise ratio) is an indicator for quantitatively evaluating an accuracy of a reconstruction result and is defined as follows. The larger a PSNR value, the higher the accuracy (the closer to quality of still image pickup).

$$\text{PSNR} = 20 \times \log_{10}(\text{MAXI}/\sqrt{\text{MSE}})[\text{dB}]$$

MAXI=Maximum value of reconstruction result of still image pickup

Figure 14G:
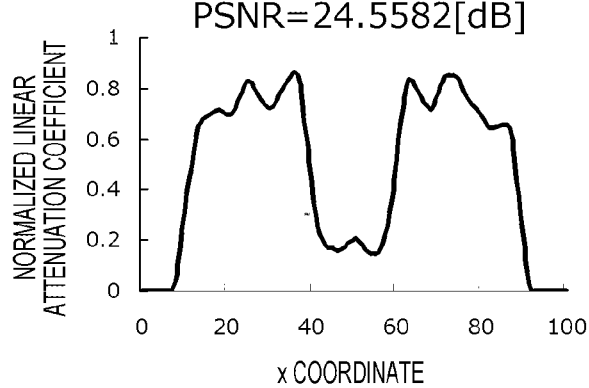

MSE=(Σ(reconstruction result of still image pickup−reconstruction result of consecutive image pickup)²)/number of pixels When motion blur correction is not performed, the quality of the reconstruction result declines significantly due to the effect of a motion blur as shown in FIGS. 14C and 14F. In comparison, it is confirmed that, by applying the motion blur correction according to the present embodiment, a reconstruction result similar in quality to still image pickup is obtained as shown in FIGS. 14D and 14G. In addition, compared to the PSNR value of 14.5751 [dB] when motion blur correction is not performed, it is confirmed that the PSNR value when applying the motion blur correction according to the present embodiment is 24.5582 [dB], which represents a significant improvement.

OTHER EMBODIMENTS

The description of the embodiment given above is merely an exemplary description of the present invention. The present invention is not limited to the specific mode described above and various modifications can be made without departing from the scope of technical concepts of the invention.

For example, while the filtered back projection method is used in the embodiment described above, another reconstruction algorithm may be used instead. As long as the algorithm includes an operation of a back projection from a transmission image to a reconstructed image, a high-quality reconstruction result with minimal blur can be obtained by applying the motion blur correction according to the present invention.

REFERENCE SIGNS LIST

1 CT system
10 Image pickup apparatus
11 Control apparatus
12 Image processing apparatus
30 Transmission image acquiring unit
31 Reconstruction processing unit
32 Parameter storage unit
33 Filter generating unit
34 Filtering unit
40, 41 Transmission image
50, 60 Reconstructed image
100, 150 Light source
101, 151 Detector
102, 152 Object
103 Electromagnetic wave
140 Model
141 Cavity

The invention claimed is:

1. An image processing apparatus, comprising:
    a transmission image acquiring unit configured to acquire data of a plurality of transmission images obtained by, while relatively moving an image pickup system comprising a light source and a detector, and an object, picking up images of an electromagnetic wave having been transmitted through the object with the detector a plurality of times; and
    a processor configured to perform operation as a reconstruction processing unit configured to perform a reconstruction process of generating a reconstructed image of an inside of the object from the plurality of transmission images, wherein
    operation as the reconstruction processing unit includes operation as a filtering unit which applies, when performing an operation of back-projecting a pixel on the transmission images to a cell on the reconstructed image, a filter for correcting a motion blur attributable to the relative movement of the image pickup system and the object to the transmission images, and wherein
    characteristics for correcting motion blurs are different between a filter that the filtering unit uses when a pixel on a first transmission image is back-projected to a first cell on the reconstructed image and a filter that the filtering unit uses when the pixel on the first transmission image is back-projected to a second cell existing at coordinates that differ from those of the first cell.

2. The image processing apparatus according to claim 1, wherein
    characteristics for correcting motion blurs are different between a filter that the filtering unit uses when a pixel on the first transmission image is back-projected to the first cell and a filter that the filtering unit uses when a pixel on a second transmission image that differs from the first transmission image is back-projected to the first cell.

3. The image processing apparatus according to claim 1, wherein
    the plurality of transmission images are picked up by changing image pickup conditions comprising a relative positional relationship and a relative movement between the image pickup system and the object, and
    the filtering unit switches filters to be used in accordance with a combination of the image pickup conditions of a transmission image and coordinates of a cell that is a back projection destination.

4. The image processing apparatus according to claim 3, further comprising a storage unit configured to store a plurality of filters associated with combinations of image pickup conditions and coordinates of cells, wherein
    the filtering unit acquires a filter to be applied to a transmission image from the storage unit on the basis of image pickup conditions of the transmission image and coordinates of a cell that is a back projection destination.

5. The image processing apparatus according to claim 1, wherein
    the reconstruction process is a process using a filtered back projection method.

6. An image processing method executed by a computer, the method comprising the steps of:
    acquiring data of a plurality of transmission images obtained by, while relatively moving an image pickup system comprising a light source and a detector, and an object, picking up an image of an electromagnetic wave having been transmitted through the object with the detector a plurality of times; and
    performing a reconstruction process of generating a reconstructed image of an inside of the object from the plurality of transmission images, wherein
    a filtering process of applying a filter for correcting a motion blur attributable to the relative movement of the image pickup system and the object to the transmission images is performed when performing an operation of back-projecting a pixel on the transmission images to a cell on the reconstructed image in the reconstruction process, and
    characteristics for correcting motion blurs are different between a filter that is used in the filtering process when a pixel on a first transmission image is back-projected to a first cell on the reconstructed image and a filter that is used in the filtering process when the pixel on the first transmission image is back-projected to a second cell existing at coordinates that differ from those of the first cell.

7. A non-transitory computer readable medium storing a program causing a computer to execute the image processing method according to claim 6.

* * * * *